(12) United States Patent
Levitan et al.

(10) Patent No.: US 8,798,732 B2
(45) Date of Patent: Aug. 5, 2014

(54) APPARATUS, SYSTEM AND METHOD OF DETERMINING A HEART RATE VARIABILITY VALUE

(75) Inventors: Jacob Levitan, Herzliya Pituach (IL); Roi Kobo, Netanya (IL)

(73) Assignee: Lev-El Diagnostics of Heart Diseases Ltd., Kibbutz Shefayim (IL)

( * ) Notice: Subject to any disclaimer, the term of this patent is extended or adjusted under 35 U.S.C. 154(b) by 0 days.

(21) Appl. No.: 13/195,880

(22) Filed: Aug. 2, 2011

(65) Prior Publication Data

US 2012/0197148 A1    Aug. 2, 2012

Related U.S. Application Data

(60) Provisional application No. 61/370,822, filed on Aug. 5, 2010.

(51) Int. Cl.
*A61B 5/04* (2006.01)

(52) U.S. Cl.
USPC .......................................... 600/515; 600/509

(58) Field of Classification Search
USPC .................... 600/508–509, 515–518
See application file for complete search history.

(56) References Cited

U.S. PATENT DOCUMENTS

| | | | |
|---|---|---|---|
| 4,018,219 A | 4/1977 | Hojaiban | |
| 4,905,708 A | 3/1990 | Davies | |
| 5,201,321 A | 4/1993 | Fulton | |
| 5,291,400 A * | 3/1994 | Gilham | 600/509 |
| 5,333,615 A | 8/1994 | Craelius et al. | |
| 5,560,368 A | 10/1996 | Berger | |
| 5,682,901 A | 11/1997 | Kamen | |
| 5,755,671 A | 5/1998 | Albrecht et al. | |
| 5,769,793 A | 6/1998 | Pincus et al. | |
| 6,026,320 A | 2/2000 | Carlson et al. | |
| 6,144,878 A | 11/2000 | Schroeppel et al. | |
| 6,731,974 B2 * | 5/2004 | Levitan et al. | 600/515 |
| 2001/0008954 A1 | 7/2001 | Levitan et al. | |
| 2005/0143668 A1 * | 6/2005 | Lu et al. | 600/509 |
| 2006/0247548 A1 | 11/2006 | Sarkar et al. | |
| 2009/0137915 A1 * | 5/2009 | Childre et al. | 600/515 |

FOREIGN PATENT DOCUMENTS

DE    4320519 A1    1/1995

OTHER PUBLICATIONS

International Search Report for PCT application PCT/IL2011/000626 mailed on Dec. 19, 2011.
International Search Report for PCT application PCT/IL01/00051 mailed on Aug. 14, 2001.

(Continued)

*Primary Examiner* — Catherine Voorhees
(74) *Attorney, Agent, or Firm* — Shichrur & Co.

(57) ABSTRACT

A system for measuring heart rate variability (HRV) comprising 3 sub-systems: a data collection sub-system, a data analysis sub-system, and an output sub-system. A patient is connected to a heart monitoring device such as an ECG and the data collection sub-system records the patients heart beats, and an ECG chart is produced from which the patient's HRV value is derived by the data analysis sub-system. The present invention obtains the HRV value through calculation of a new parameter called relative density (RD). In accordance with the inventive method, data points are generated from the peak interval data of measured heart beats and the HRV relative density parameter (RD) is calculated by correlation between two subsets of data points.

20 Claims, 7 Drawing Sheets

(56) References Cited

OTHER PUBLICATIONS

Marciano et. al. "Quantification of Poincare Maps for the Evaluation of Heart Rate Variability", Computers in Cardiology, IEEE, pp. 577-580, 1994.

Hnatkova K., "Numeric Processing of Lorenz Plots of R-R Intervals From Long-term ECGs", Journal of Cardiology, vol. 28 Supplement, pp. 74-80, 1995.

Partial Search Report for European patent application 01100173.2 mailed on May 31, 2001.

Office Action for European patent application 01100173.2 mailed on Oct. 16, 2006.

Office Action for European patent application 01100173.2 mailed on Aug. 21, 2009.

* cited by examiner

| Peak Intervals | Average | Detrended Data |
|---|---|---|
| $RR_1$ | --- | --- |
| $RR_2$ | --- | --- |
| $RR_3$ | --- | --- |
| $RR_4$ | --- | --- |
| $RR_{127}$ | --- | --- |
| $RR_{128}$ | --- | --- |
| $RR_{129}$ | --- | $r_1 = RR_{129} - AVER_{257}$ |
| $RR_{130}$ | --- | $r_2 = RR_{130} - AVER_{258}$ |
| $RR_{257}$ | $AVER_{257}$ | $r_{129} = RR_{257} - AVER_{385}$ |
| $RR_{258}$ | $AVER_{258}$ | $r_{130} = RR_{258} - AVER_{386}$ |
| $RR_{259}$ | $AVER_{259}$ | $r_{131} = RR_{259} - AVER_{387}$ |
| $RR_{260}$ | $AVER_{260}$ | $r_{132} = RR_{260} - AVER_{388}$ |
| $RR_{n-128}$ | $AVER_{n-128}$ | $r_{n-256} = RR_{n-128} - AVER_n$ |
| $RR_{n-1}$ | $AVER_{n-1}$ | --- |
| $RR_n$ | $AVER_n$ | --- |

FIG. 4

| $RR_1$ | $RR_2$ | $RR_3$ | $RR_4$ | $RR_5$ | --------- | $RR_{n-2}$ | $RR_{n-1}$ | $RR_n$ |

APPARATUS, SYSTEM AND METHOD OF DETERMINING A HEART RATE VARIABILITY VALUE

BACKGROUND

1. Technical Field

Embodiments of the present invention relate generally to medical methods and, more particularly, but not exclusively, to a method for measuring heart rate variability (HRV)

2. Description of Related Art

Heart rate variability (HRV) is a well-known characteristic of heart function, and is a measure of variation in heart rate experienced by a particular patient.

Figure 1:
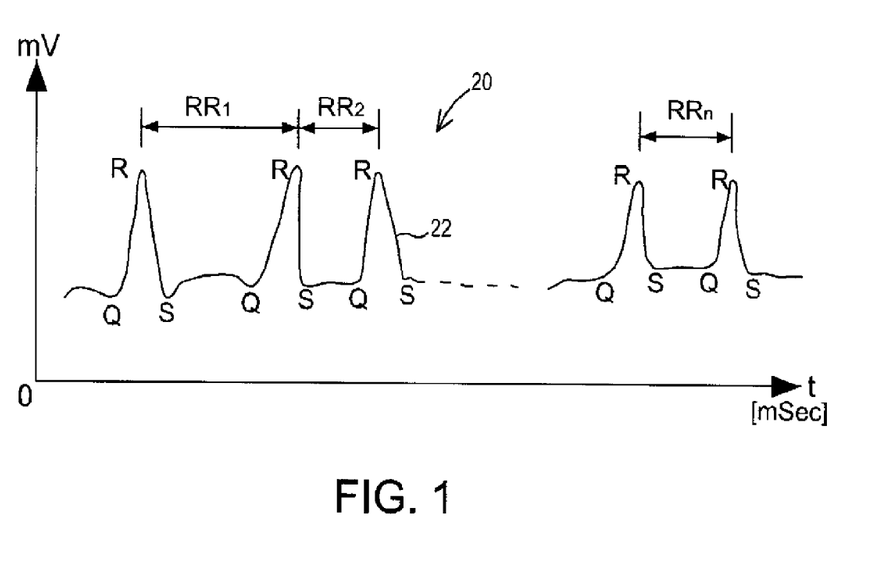
FIG. 1 is an illustration of an electrocardiograph measurement of a series of heartbeats.

HRV is usually measured as the time (in milliseconds) between successive heartbeats This time period is also known as the "beat-to-beat interval", and is the inverse of the instantaneous heart rate expressed in beats per second. FIG. 1 shows a standard ECG display of a series of heartbeats. It can be seen that each heartbeat appears as a wave, and that each wave in the series has points in common designated "Q", "R", and "S" The point "R" is the highest peak and most visually distinguishable part of the wave, and therefore the easiest point from which to measure HRV. Accordingly, the beat-to-heat intervals may be designated as "RR intervals" or "peak intervals", where "RR" is the interval between successive R's.

A patient heartbeat record will typically have thousands of heartbeats or waves. In order to extract HRV from this data, the waveforms are digitized and the RR intervals measured HRV can then be conveniently represented in visual form by plotting the RR interval data as a non-linear recurrence or Poincaré plot, in which each data point is formed from a pair of successive RR intervals. HRV can be further quantified by applying a mathematical algorithm to the data points. Some of the algorithms that have been suggested however are complicated and/or fail to produce HRV values that are reliable in clinical applications.

The heart is connected to the autonomic nervous system, and the length of an RR interval is primarily governed by inputs from this system's two main components: the sympathetic nervous system and the parasympathetic nervous system. These latter two inputs to the heart are timed independently of one another in the normal course, and are also influenced by unrelated external factors such as the baroreceptor reflex, thermo-regulation, hormones, the sleep-wake cycle, eating, and stress. Accordingly, a certain degree of heart rate variability is to be expected in a healthy individual, and is a reflection of a well functioning autonomic nervous system. Similarly, a heart rate variability that is lower or otherwise different from the norm is often an indication of a malfunctioning autonomic nervous system.

As a result of this connection, HRV is often used in clinical settings to estimate the efferent autonomic activity to the heart and the integrity of this part of the cardiovascular control system. Problems with the autonomic nervous system are also associated with a variety of other medical conditions, such as, for example, congestive heart failure, Parkinson's disease, diabetic neuropathy, and Alzheimers. Accordingly, an HRV reading can suggest a risk of the patient acquiring such a condition in the future, or alternatively help evaluate the severity and progress of the condition where the patient has already been diagnosed.

HRV is also used to help evaluate and determine a course of treatment for patients who have had a serious heart attack, such as acute myocardial infarction (AMI). Post heart attack patients are at risk of ventricular tachycardia (VT), a fast heart rhythm that originates in a heart ventricle. VT is a potentially life-threatening arrhythmia that may lead to ventricular fibrillation (VF) and sudden death. This combination of a VT episode followed by VF is sometimes referred to as "VT/VF".

Patients considered to be at risk of VT/VF are often treated by receiving a surgically implanted device called an implantable cardioverter defibrillator (ICD). An ICD is a small, battery powered electrical impulse generator that continuously monitors a patient's heart rate and delivers a small electric jolt or shock when it detects a cardiac arrhythmia such as VT or VF. In some cases, instead of applying a shock, an ICD that detects VT will pace the heart at a faster rate, to break up the VT before it progresses to VF. A problem with ICD's however is that they sometimes respond to the arrhythmia too late, causing neurological damage or death. Another problem is that the ICD electric shocks, even if appropriately delivered, are painful and often unexpected by the patient. Yet another concern is simply the risk that is always present for a procedure that involves surgery.

An alternative therapeutic approach to VT/VF risk is to suppress an episode from occurring by putting the patient on long term anti-arrhythmic drugs such as beta-blockers or amiodarone. These drugs however are costly and have potent side effects.

The drawbacks of available therapies suggest the importance of obtaining an accurate diagnosis of a patient's post AMI risk for VT/VF. A patient that is wrongly diagnosed as low risk and that accordingly doesn't receive an ICD or drug treatment has a high likelihood of experiencing a fatal heart attack Conversely, a patient that is wrongly diagnosed as high risk will experience some level of pain, trauma, cost, and/or surgical risk if implanted with an ICD or prescribed a drug unnecessarily. Physicians who evaluate a patient's post AMI risk for VT/VF sometimes consider the patient's HRV value, in combination with other factors, in making their decision. However, there continues to be an excessive variation among different practitioners in the effective rate of ICD implantation and appropriate drug therapy, in part due to inadequate risk stratification.

BRIEF SUMMARY

According to an aspect of the present invention, there is provided a method for measuring heart rate variability (HRV), the method comprising:

recording electrocardiograph measurements for a series of heartbeats;

determining peak interval data from the electrocardiograph measurements.

generating a plurality of data points from the peak interval data;

identifying two subsets of data points from the plurality of data points, each subset having a maximum number of data points, and calculating an HRV relative density parameter (RD) by dividing the maximum number of data points in one of the two subsets of data points by the maximum number of data points in the other one of the two subsets of data points.

According to another aspect of the present invention, there is provided a method for providing heart treatment in real time, the method comprising:

recording an electrocardiograph measurement of a current heartbeat;

measuring an interval between the current heartbeat and a preceding heartbeat;

adding the measured interval to a record of a series of intervals corresponding to a series of preceding heartbeats;

calculating a heart rate variability (HRV) parameter based upon a predetermined number of recorded intervals; and applying a heart treatment if the HRV parameter exceeds a threshold.

According to yet another aspect of the present invention, there is provided a system for measuring heart rate variability (HRV), the system comprising:

a data collector, to record heart beats and detect a series of heart beat intervals;

a data analyzer, to analyze the series of heart beat intervals and obtain an HRV value based on a relative density parameter; and an output device, to output the HRV value.

According to yet another aspect of the present invention, there is provided a method for measuring heart rate variability (HRV), the method comprising:

collecting electrocardiograph measurements for a series of heartbeats;

determining peak interval data from the electrocardiograph measurements;

discarding peak interval data having a length greater than 2500 msec;

generating a plurality of data points from the peak interval data, each data point having a first coordinate on a first axis and a second coordinate on a second axis;

translating each data point to a new data point having a new first coordinate and a new second coordinate according to the formula:

new first coordinate=cos 45(first coordinate plus second coordinate), and new second coordinate=cos 45(second coordinate minus first coordinate);

selecting a data interval length;

shifting and expanding each new data point according to a multiple of the data interval length;

identifying a first data interval on the first axis having a first maximum number of data points, and a second data interval on the second axis having a second maximum number of data points;

calculating an HRV relative density parameter (RD) by dividing one of the first or second maximum number of data points by the other of the first or second maximum number of data points.

These, additional, and/or other aspects and/or advantages of the present invention are set forth in the detailed description which follows; possibly inferable from the detailed description, and/or learnable by practice of the present invention.

BRIEF DESCRIPTION OF THE DRAWINGS

The present invention will be further understood and appreciated from the following detailed description taken in conjunction with the drawings in which.

DETAILED DESCRIPTION

Reference will now be made in detail to embodiment(s) of the present invention, examples of which are illustrated in the accompanying drawings, wherein like reference numerals refer to the like elements throughout. The embodiment(s) is/are described below to explain the present invention by referring to the figures.

Referring to FIG. 1, there is shown a graphic illustration of a heartbeat wave or series of waves 20, as detected by an electrocardiograph (ECG) or similar device. A "beat-to-beat interval" is the time between equivalent points on adjacent waveforms. As noted above, by convention each wave contains standard reference points "QRS". Accordingly, heartbeat waves 20 may be defined as a series of RR or peak intervals, as shown in the figure by intervals RR1, RR2, and RRn. It is to be appreciated that heartbeat intervals could also be measured with respect to any other equivalent points on the wave, such as the points "Q" and "S", for example. For convenient reference, the series or stream of peak interval values RR1, RR2, to RRn may be designated as interval stream 22.

The term "Heart Rate Variability" ("HRV") refers to the amount by which the beat-to-beat intervals vary for a particular patient. The analysis may be conducted from data samples of differing duration, such as, for example, samples as short as fifteen minutes or as long as forty-eight hours. Accordingly, a given data sample will typically contain thousands of waveforms. Most intervals between adjacent heartbeats will fall between 500 to 1500 msec, with a smaller number of exceptions falling outside of this range.

In practice, it is difficult to assess a patient's HRV from visual inspection of the raw waveform data. The present invention provides a novel method of analysing and quantifying this information, to obtain a characteristic HRV value useful for clinical assessment. The method introduces a new parameter "RD", which is calculated based on a relative density of data points.

In addition, in some embodiments the present invention may be configured to provide an output HRV value in real time, to aid in immediate or emergency treatment of certain patient conditions. In particular, in some embodiments the present invention may be used in an ICD to detect an imminent episode of VT at a point in time before the onset of the episode. In this way, the patient may receive an early alert well before the VT, and certain treatments may be applied that would not otherwise be possible.

Figure 2:
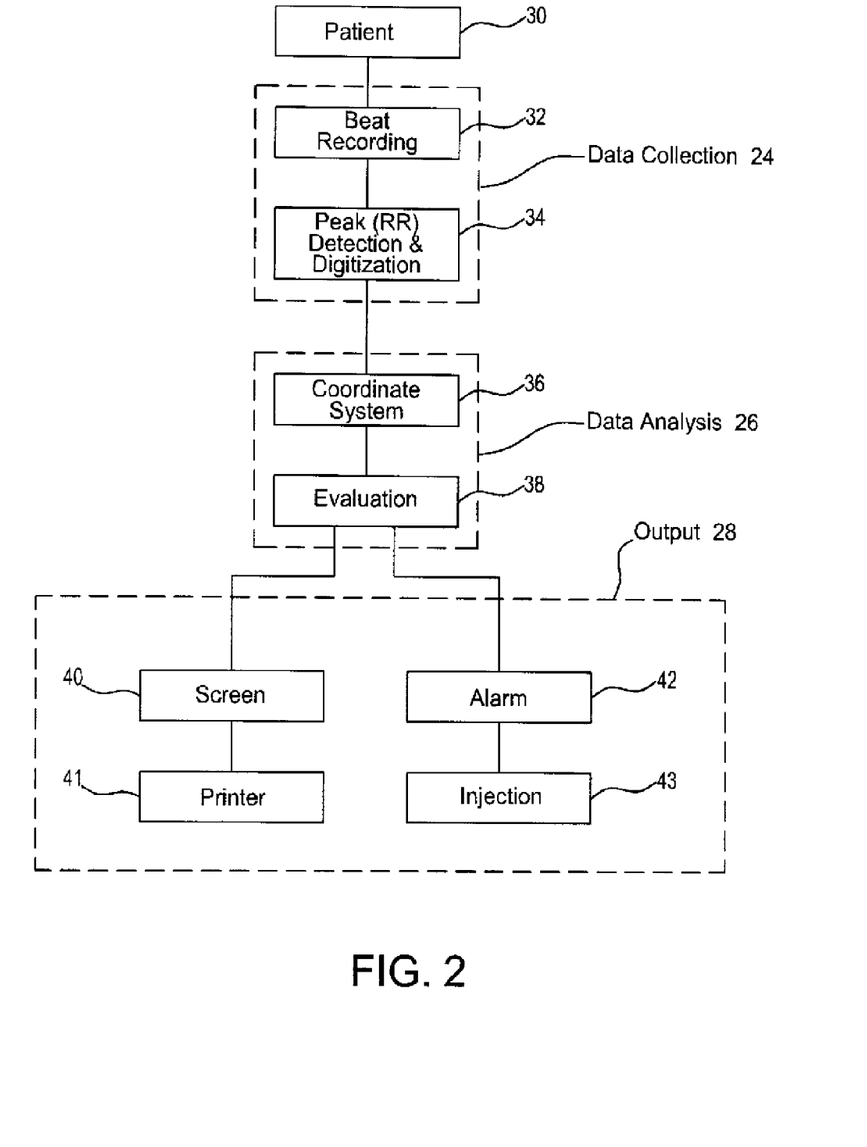
FIG. 2 is a block diagram of a system for measuring heart rate variability, consistent with an embodiment of the present invention.

FIG. 2 shows a block diagram of a system for measuring heart rate variability, consistent with an embodiment of the present invention. The system has three parts or subsystems: a data collection subsystem 24, a data analysis subsystem 26, and an output subsystem 28. A patient, represented as module 30, is connected to a heart monitoring device such as an ECG. In data collection subsystem 24 the patient's heartbeats are first recorded (module 32), to produce the ECG chart shown in FIG. 1. Subsequently, in digitization/detection module 34, the analog waveform is digitized and its associated peak intervals are detected or measured. Accordingly, the output of data collection subsystem 24 is interval stream 22, i.e. the series of interval values RR1, RR2, ... RRn shown in FIG. 1.

In data analysis subsystem 26, interval stream 22 is first converted into a two-dimensional co-ordinate system by coordinate conversion module 36. Optionally, further mathematical conversions and transformations may be applied to the data to enhance analysis or visualization, and a recurrence plot may optionally be displayed. Module 38 evaluates the coordinate data using the analysis method of the present invention to obtain the patient's HRV value.

Output subsystem 28 shows a variety of outputs that may be implemented, individually or in combination, according to different embodiments of the invention. As shown, the resulting HRV value may be displayed on a computer screen (module 40) or printed (module 41). Alternatively or additionally the HRV value may trigger an alarm (module 42) and/or lead to application of a treatment such as drug injection (module 43). The latter two results, alarm and injection, are more likely to be used in embodiments where the present invention is used for real time or immediate/emergency treatment.

Figure 3:
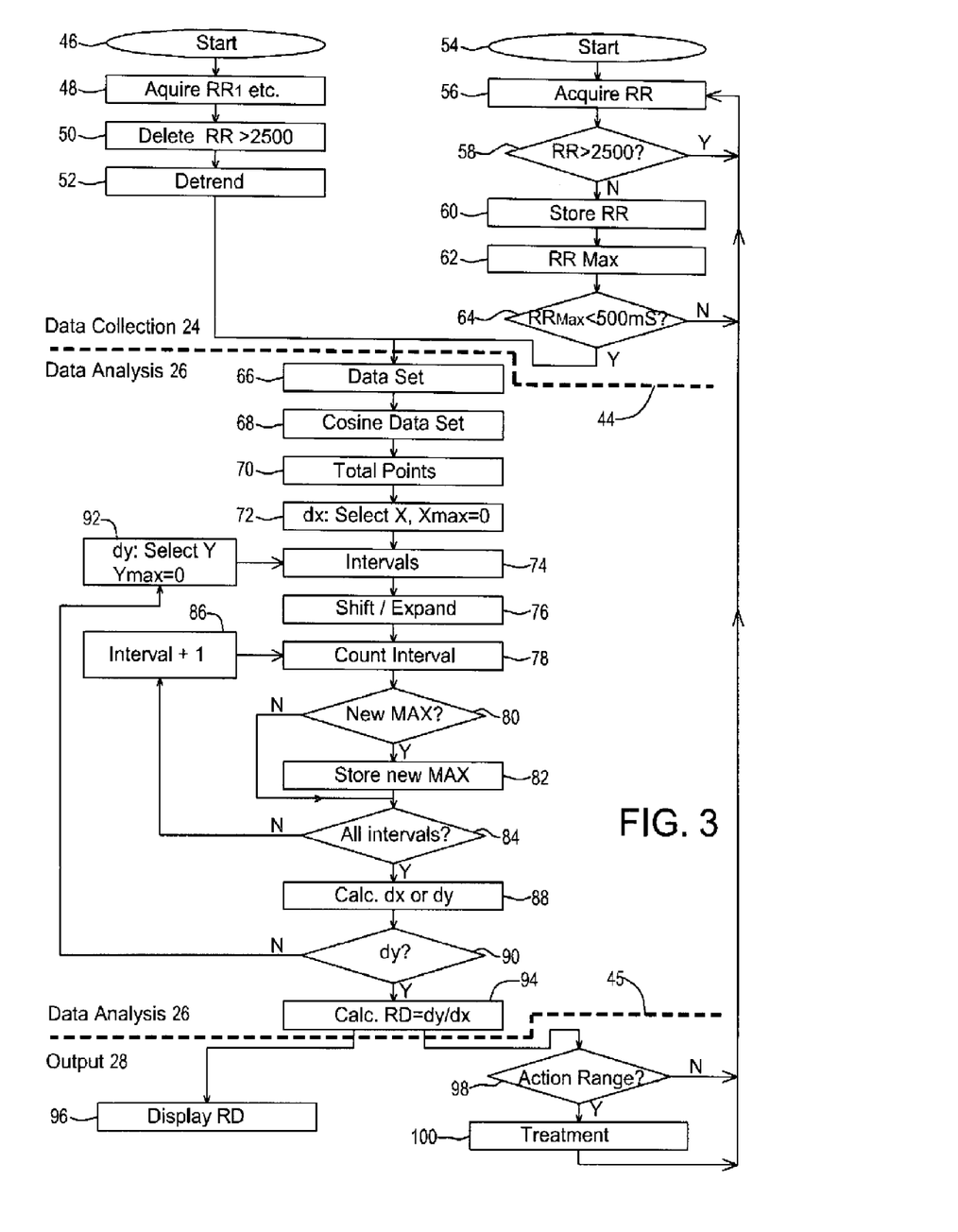
FIG. 3 is a block diagram of a method for measuring heart rate variability, consistent with an embodiment of the present invention.

FIG. 3 shows a block diagram of a method for measuring heart rate variability, consistent with an embodiment of the present invention. The figure includes dashed lines 44 and 45 to indicate the correspondence of the figure with the three subsystems of the invention shown in FIG. 2. As indicated, the first and third subsystems each have modules located on a left side and a right side, to correspond with different embodiments of the invention. The right side modules refer to some embodiments in which the HRV value is used to provide immediate or real-time medical treatment.

Beginning with data collection subsystem 24, on the left side, the method begins at start module 46. Module 48 collects, digitizes, and detects the heartbeat information to obtain interval stream 22. In module 50 peak intervals that are unusually long, as measured in comparison with a predetermined high threshold, are deleted from the interval stream. These intervals are discarded because they are likely to be artifacts or aberrations in the data, and could accordingly lead to distorted results. It has been found that 2500 msec is an adequate nigh threshold value, but other values may also be used according to the situation.

In module 52 the interval data is "detrended" by calculating an average and subtracting the average from the peak interval data points. Detrending is applied to smooth out from the data any variations caused by sudden jumps in heart rate that may occur in connection with ordinary daily activities such as, for example, a sudden movement like standing up quickly, running, eating, or coughing. The detrending calculation may be based on any of the various averaging techniques known in the art.

Figure 4:
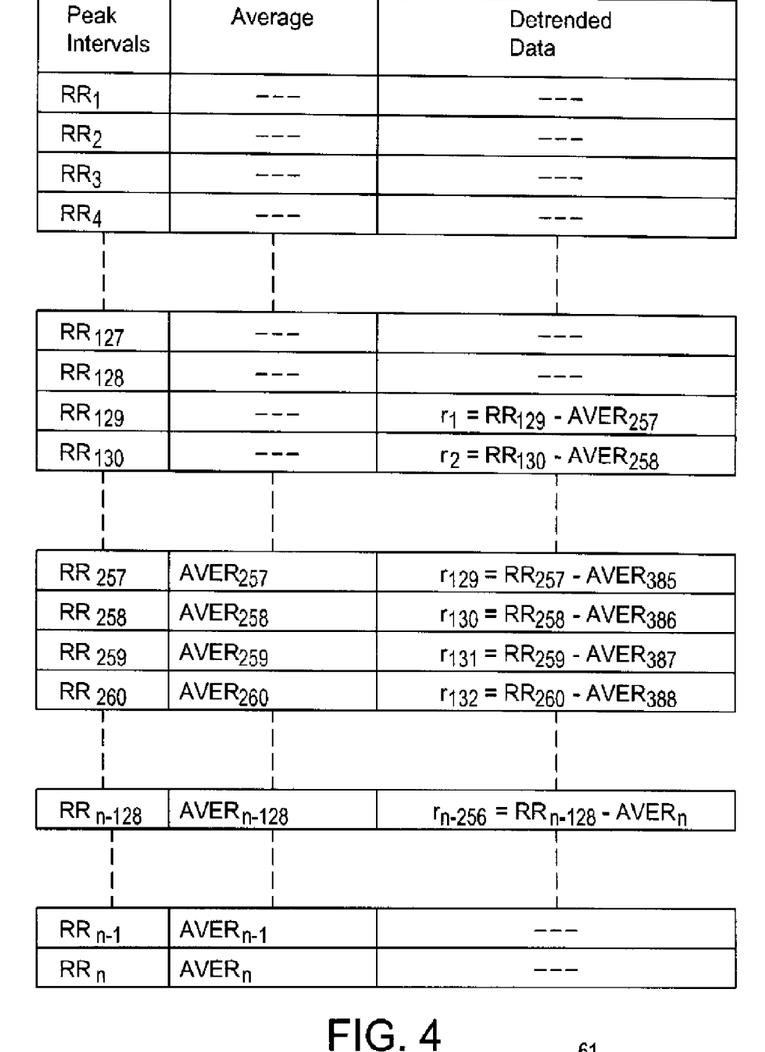
FIG. 4 is a table illustrating the detrending of peak interval data, consistent with an embodiment of the present invention.

FIG. 4 is a table that illustrates one example of a detrending algorithm that has been found to be adequate for interval stream data. The first column in the table is the raw data of interval stream 22, i.e. peak intervals from RR1 to RRn. The second column indicates that an average is taken over every 257 points. Accordingly, the first average capable of full calculation applies for interval RR257. This parameter is represented by the term "AVER257", and represents an average of all data points from RR1 to RR257. Similarly, the next data point RR258 has an associated AVER258 that represents the 257 points from RR2 to RR258. In this way, an average is calculated for all remaining data points up to RRn. In the third column of the table, the detrended data is calculated by subtracting an average value of column two from an original interval value of column one. As shown, the first data point "r1" occurs with respect to RR129, and is calculated by subtracting AVER257 from RR129. The detrending of a particular data point accordingly involves subtracting an average that spans data points encompassing a range from 128 points before to 128 points after the data point of interest. In this way, module 52 smooths out from the data sudden spikes in the heartrate due to influences unrelated to the autonomic nervous system.

Returning to FIG. 3, on the right side, start module 54 denotes the beginning of data collection for embodiments of the present invention capable of providing real time treatment. In module 56 a single data point, i.e. the value of a peak or RR interval, is acquired Decision module 58 queries if this value exceeds a predetermined high threshold, such as 2500 msec. If the threshold is exceeded, the just-acquired peak interval is discarded and control returns to module 56 to acquire the next peak interval value. Otherwise, if the value is below the high threshold, the acquired peak interval value is stored in memory according to module 60.

Figure 5:
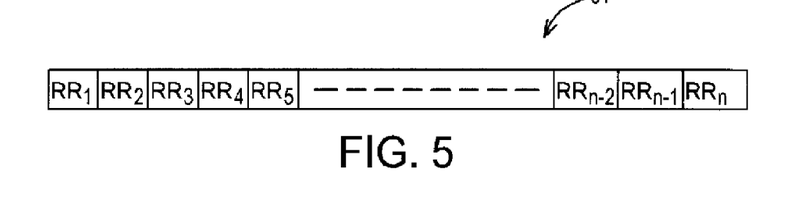
FIG. 5 is a schematic diagram illustrating storage of peak interval values in the memory of an electrocardiograph recording device.

FIG. 5 is a logical representation of a computer memory 61 showing how the values of interval stream 22 may be stored at a given time. Peak interval RR1 is the oldest value and interval RRn is the most recent acquired value. In this logical representation, each subsequent acquired peak interval is stored adjacent to, or to the right of RRn.

The remaining two modules of data collection subsystem 24 apply a sub-algorithm that is useful as a preliminary test for embodiments that provide real time treatment. One type of test is to look for an acceleration or rise in the patient's pulse or heartrate above a specified threshold. Only after the sub-algorithm finds the heartrate exceeding the threshold is the subsequent HRV calculation taken into account. An example of a test that has been found to be adequate for the sub-algorithm is a period of ten consecutive heartbeats in which the pulse rate is 120 beats per minute or greater. Since the peak intervals are expressed in milliseconds and are the inverse of the heart rate, this pulse figure can be shown to correspond to a peak interval value of 500 milliseconds or less.

Using the above sample test parameters, after the newest interval value is stored in memory at module 60, the most recent ten values in memory (i.e. RRn to RRn-9) are examined and the highest value in this group is recorded at module 62 as RRmax. Decision module 64 then queries if RRmax is less than or equal to 500 milliseconds. In effect, this test is equivalent to checking if the most recent ten heartbeats are all above 120 beats per minute. If the answer is no, as will most often be the case, control returns to module 56 and the next peak interval value is acquired. Where the pulse rate has increased past the threshold, the recorded interval stream 22 stored in memory 61 as of that point in time is passed to data analysis subsection 26.

In some embodiments of the invention, the preliminary test of modules 62 and 64 may be omitted. In such cases, an HRV value would always be available, and would be updated continuously as each incremental addition to the interval stream is received and stored in memory.

In the embodiments for real time treatment the data is not detrended, as this was not found to be as useful in this application. However, detrending may optionally be applied in these embodiments as well if found to be appropriate.

In the embodiments for real time treatment, the particular preliminary test that is applied relates to the cardiac condition which is desired to be treated by the present invention. For example, the sample preliminary test described above, i.e. an acceleration or rise in heartbeat to the point where ten consecutive beats have a pulse rate of 120 beats per second or greater, is an event that in some cases precedes episodes of VT. It is to be appreciated that in other embodiments that treat VT, a test having different parameters other types of test may be used. Similarly, where the present invention is used to treat other cardiac conditions, different preliminary tests of the stored interval stream than the one described above may alternatively be used.

Turning now to data analysis subsystem 26 of FIG. 3, module 66 receives interval stream 22 and converts the series of peak intervals into a two-dimensional "x-y" coordinate system. In some embodiments, adjacent peak interval pairs are mapped into coordinates by setting the first peak interval in the pair to be the abcissa or "x" axis point, and the second peak interval pair to be the ordinate or "y" axis point. The next peak interval pair has as its first interval the second interval from the previous peak interval pair. For example, according to this method the first four intervals of interval stream 22, i.e. RR1, RR2, RR3, and RR4, transform into the following three coordinates: (x1,y1)=(RR1,RR2), (x2,y2)=(RR2,RR3), and (x3,y3)=(RR3,RR4).

Figure 6:
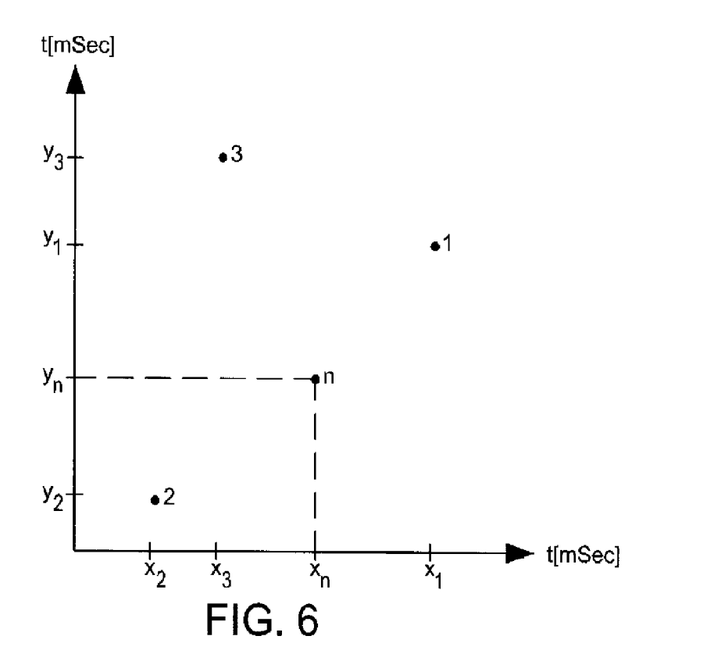
FIG. 6 is an illustration showing charting of a small sample of data points that form a recurrence or Poincaré plot, consistent with an embodiment of the present invention.
Figure 7:
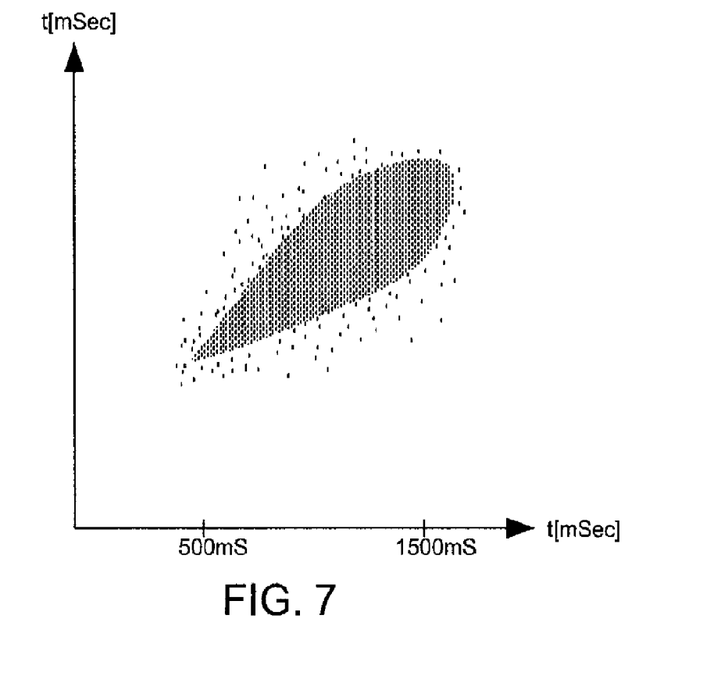
FIG. 7 is an illustration of a completed recurrence or Poincaré plot of data points, consistent with an embodiment of the present invention.

The data coordinates generated by module 66 may optionally be plotted to form a recurrence chart. FIG. 6 shows the plotting of an initial set of four sample data points. It is to be appreciated that since each peak interval in interval stream 22 is independent of the others, any particular abcissa Xn may be greater or lesser than the preceding abcissa Xn−1, and the recurrence plot is accordingly nonlinear. FIG. 7 shows a sample recurrence chart made up of all the data points that is characteristic of healthy individuals without severe pathologies. As indicated, the plot has a "cigar" shape and an orientation of about 45 degrees, with most points falling between 500 to 1500 msec interval times.

The data coordinate points established in module 66 may optionally be further modified or transformed by mathematical module 68. By way of non-limiting example, in some embodiments of the invention a new coordinate set (Xnew, Ynew) is calculated according to the formula:

$$X\text{new} = \cos 45 (Xn + Yn), \text{ and}$$

$$Y\text{new} = \cos 45 (Yn - Xn).$$

Figure 8:
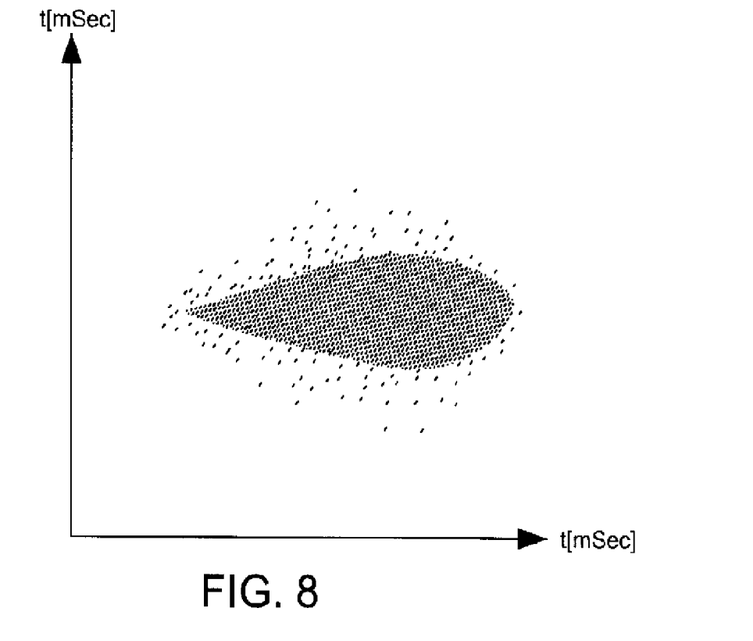
FIG. 8 is an illustration of the recurrence plot of FIG. 7 to which a cosine function has been applied, consistent with an embodiment of the present invention.

As shown in FIG. 8, the effect of this transformation is to rotate the plot of FIG. 7 by approximately −45 degrees so that plot becomes substantially flattened, or parallel to the time axis. An advantage of this transformation is that it represents the data in a more convenient form, in which the data values are normalized between 0 and 1. Optionally, module 68 may provide a visual display of the transformed plot.

The present invention obtains HRV through calculation of a new parameter called Relative Density ("RD"). RD is a quotient of two factors, "dx" and "dy", where "x" refers to an x-axis or abcissa and "y" refers to a y-axis or ordinate. In calculating dx and dy, each axis is divided into an arbitrary number of data intervals. The number of data points in each data interval is counted, and the maximum number of points in a data interval for each axis is recorded. The factor dx is assigned the value of this maximum number for x-axis intervals divided by the total number of data points, and dy is similarly calculated based on the maximum number for y-axis intervals.

The set of (x,y) data points are first received by module 70, which counts the total number of points in the set, and stores the value for subsequent use. As will be discussed further below, module 70 is optional as it is not necessary for the calculation of RD.

Assuming that dx is obtained first, for example, module 72 selects the "x" axis or abcissa, and initializes a parameter Xmax to zero. Xmax is used to store the number of data points in the data interval along the x-axis having the most (i.e. "maximum") number of data points.

Module 74 selects "h", a parameter used to designate a data interval length. The interval length is selected to be a value large enough to contain a meaningful sample of data points, but small enough to allow a reasonable number of intervals. For example, where the data points along a given axis are between 0 and 1, an interval length h of 0.05, that divides the axis into twenty equal data intervals, may be adequate. Alternatively, and in particular as shown in the discussion of module 76 below, where the data points fall along a larger range, interval length h may be set at a correspondingly larger nominal value.

Figure 9:
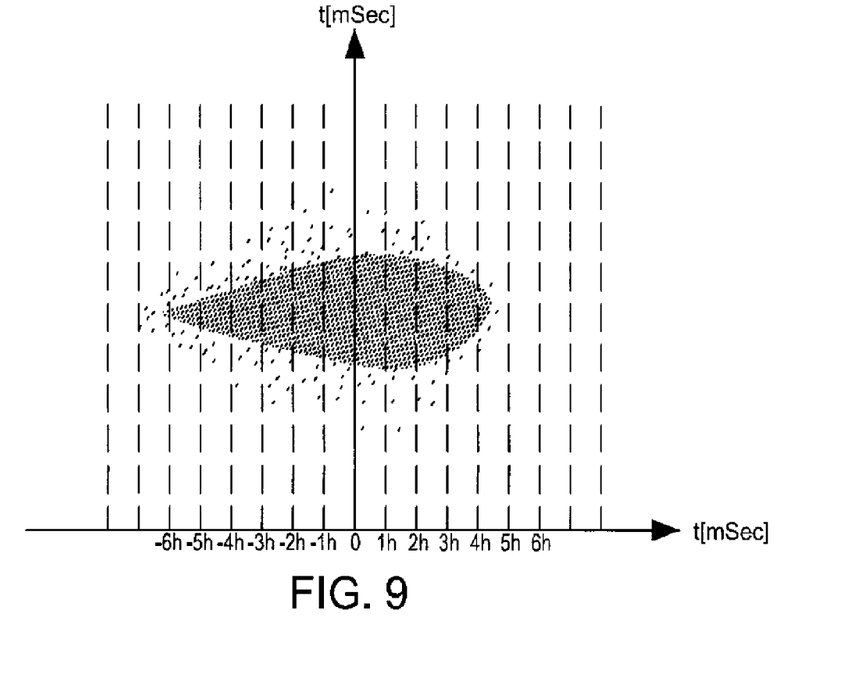
FIG. 9 is an illustration of the recurrence plot of FIG. 8 to which a shift and expansion has been applied, consistent with an embodiment of the present invention.

Module 76 optionally shifts and/or expands the data set along the given axis so that the axis may be more easily divided into visually distinct intervals having a relatively large data interval length "h". Shifting of the data set may be performed by translating each point so that approximately half the data points fall on a negative side and approximately half fall on a positive side of the axis. The data set may be expanded by multiplying each of the coordinates on a particular axis by a multiplier. When this is done, the axis may be considered to extend from −20 h to +20 h. By way of non-limiting example, select a data interval h=13 and a multiplier of 20, so that 20 h is 260. The new axis scale accordingly ranges from minus 260 to +260, and is divided into equal data intervals of length 13, i.e. 13, 26, 39 . . . and −13, −26, −39 etc. Data points are multiplied by 20, so for example, a data point falling on the axis at −0.3 becomes −6, a point at +0.74 becomes +14.8, etc. An illustration of how the method of the present invention divides an axis into data intervals "h" is shown in FIG. 9. As indicated, the data set is usually shifted along the x-axis, and the same data interval "h" is applied to both the x-axis and the y-axis.

Module 78 counts the number of data points in the current interval. The module is initialized to start at the first interval. Decision module 80 then queries if the data point count in the current interval is a new maximum. If it is a new maximum, module 82 assigns Xmax this data point count. Since Xmax was initialized at zero, upon reading the first interval Xmax will always acquire the value of data points in that interval. Otherwise, if the current data interval does not have a new maximum number of data points, control skips over module 82 to decision module 84.

Decision module 84 queries if all intervals have been counted. For example, where the range is 20 h, decision module 84 checks if all 40 intervals from −20 h to +20 h have been counted. If not, control passes to module 86 which increments an interval counter by one, and the next interval data points are counted at module 78. Otherwise, when all intervals along an axis have been counted, control passes to module 88. The factors dx and dy are calculated in module 88 by dividing Xmax or Ymax, as the case may be, by the total number of data points obtained from module 70.

Decision module 90 queries if the value of parameter dy has been obtained. If not, control passes to module 92 which selects the y-axis and sets Ymax to zero. The factor dy is then calculated, beginning at module 74, in the same manner as that used to obtain dx. In some embodiments the function of module 92 may be incorporated into module 72, so that module 72 selects either the x-axis or y-axis and sets Xmax or Ymax to zero, as appropriate. In such a case, control from decision module 90 on a negative result would go to module 72.

Upon calculation of dy, module 94 calculates RD by dividing dy by dx, or optionally, dx by dy. In some embodiments it has been found convenient to divide dy by dx, so that RD=dy/dx. This is the case because dy is usually larger than dx, and RD calculated this way results in a number that is conveniently greater than one. An RD value that is, for example, the number "2.3" rather than its inverse "0.43478", is likely to be perceived as easier to work with by clinicians in the field. It is also to be appreciated that since the total number of data points obtained in module 70 is the divisor of both factors dy and dx, this total figure cancels out when the factors are divided. For this reason, as noted above, obtaining the total number of points is optional and may be skipped in some embodiments.

Figure 10:
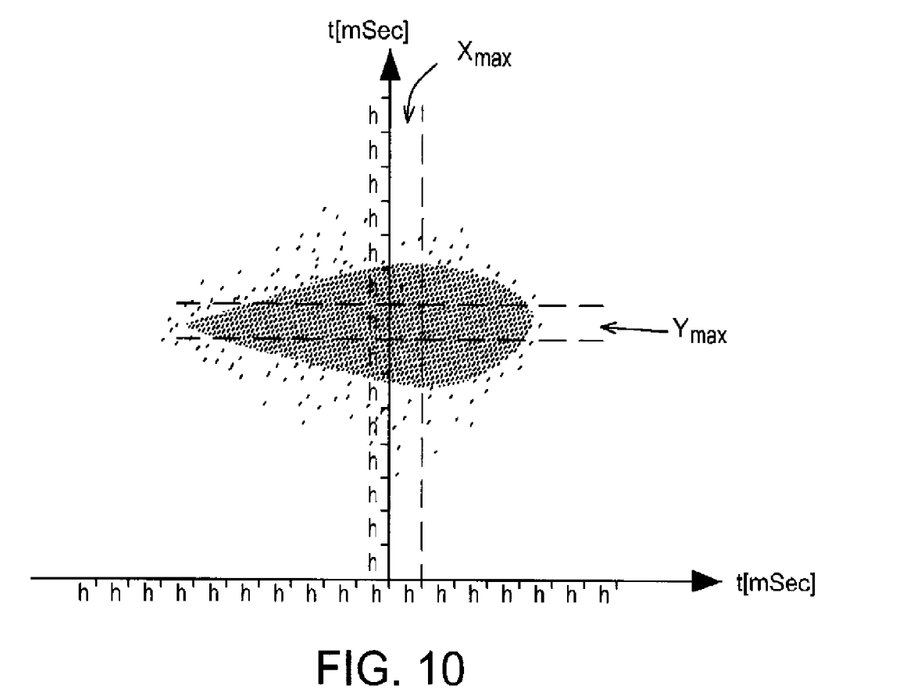
FIG. 10 is an illustration of a recurrence plot showing sample data intervals used in the calculation of the relative density parameter, consistent with an embodiment of the present invention.

FIG. 10 shows a graphical representation of the method of the present invention. There is shown a recurrence plot in which the x-axis and y-axis are divided into a series of equal intervals of length "h". On the x-axis a particular interval "h" is identified that contains Xmax, the maximum number of data points for any x-axis interval. Similarly, on the y-axis an interval "h" is identified that contains Ymax, the maximum number of data points for any y-axis interval. According to the present invention. HRV is the relative density parameter, or RD, that is equal to the ratio of Ymax to Xmax (or its inverse).

Returning to FIG. 3, the calculated RD value is output from module 94 and enters output subsystem 28. In some embodiments the RD value may be displayed, such as on a computer screen, as shown by module 96 on the left side of output subsystem 28. An attending physician or clinician may read the displayed value and provide an appropriate diagnosis to the patient. In practice, the RD value may alternatively be stored, emailed, or printed, for later analysis at a later time with or without the patient in attendance.

Where the HRV application includes real-time treatment, the RD value is received by decision module 98, as shown on the right side of output subsystem 28. Module 98 queries if RD falls within a range of predetermined values that have been found to indicate that a dangerous medical or cardiac condition, such as VT, may occur. If RD does not fall in the designated range, control is passed back up to module 56, to acquire a new peak interval and repeat the process of FIG. 3. The process continues because, as noted, in this application the present invention is being used to monitor the patient continuously and provide real-time treatment if needed. Accordingly, there is no reason to stop just because a test at a particular point in time came out negative and did not require treatment.

If RD falls within the active range at module 98, module 100 optionally applies a real-time treatment. This may include such measures as: applying a minor shock or other warning to the patient, applying a series of low-level shocks to pace the heart, applying a defillibrator level shock, injecting a drug from an implanted syringe, and/or summoning an attending medical professional. As before, after applying the treatment control is passed to module 56 at the start to continue patient monitoring.

Through repeated application and experimentation, a scale composed of several ranges of RD values may be developed for use in assessing and interpreting the obtained RD values.

For example, according to a sample scale, an RD value of 2.3 or less may indicate a patient having a relatively high risk of a cardiac problem or other medical condition, an RD value of 2.7 or higher may indicate a relatively low risk, and a value between 2.3 and 2.7 may be a gray zone, requiring further physician interpretation Different scales having different numerical ranges may be applicable in different situations according to various factors such as: the duration of the recording, the type of recording device used, and the type of diagnosis or treatment being performed. Additionally, the scale may be adjusted to obtain a desired sensitivity. For example, continuing the example above, if the high risk threshold RD value is raised from 2.3 to 2.4, more patients destined to experience VT will be correctly identified in advance, but at the same time more patients who will not experience VT will be incorrectly identified as being at risk. In the case of real time determination of imminent VT, raising the high risk threshold will catch more actual VT episodes but also increase the number of false alarms It is to be appreciated that in calculating RD, the method of the present invention uses a region of the recurrence plot that is much smaller than that used in other methods. This is possible because most heart beat intervals are located in a tight range close to the central part of the plot. The inventor was the first to realize that a simple and accurate calculation for HRV may be obtained by focusing on the data points in these densely located areas of the plot.

The method of the present invention may be operated as software on or in communication with any physical hardware device that records beat-to-beat intervals of the head. Depending on the application, this may include, for example, an ECG machine such as that used in hospitals and medical offices, a Holter or other external device worn by a patient for extended periods such as 24 hours, or an ICD.

In an example application, a patient with no prior heart condition may receive a medical checkup. The patient may be healthy, or may have a prior condition such as Parkinson's, diabetes, or Alzheimers, for example. An ECG reading may be taken as part of the checkup, and the method of the present invention applied to the recorded peak intervals to calculate the relative density, or HRV value. The physician will analyze this value relative to the applicable scale, and advise the patient accordingly. The advice may take the form of a diagnosis, i.e. that the reading indicates that the patient has a specific medical condition. In some situations the advice may take the form of a prognosis, such as that the HRV value suggests a problem with the autonomic nervous system. If the patient was otherwise considered healthy, this result suggests that a medical condition that relates to a malfunctioning autonomic system may develop at some point in the future. The physician may use this information to provide therapeutic or behavioural recommendations. If the patient was already diagnosed with a condition related to the autonomic nervous system, the result acts as confirmation and may assist in better understanding the status of the patient's condition.

In another example application, the patient may have experienced a serious cardiac incident such as, for example, an AMI. A heartbeat reading may be taken, such as by an ECG at a clinic or by a holter worn for 24 hours. The method of the present invention may again be used to analyze the data and provide an HRV value from the relative density calculation. This HRV value may be used for diagnosis of a current medical condition or for prognosis of a possible future medical condition. In this case, since the patient has had a cardiac incident, the HRV value may also be used to assist the doctor in determining the risk that the patient will have an episode of VT, leading to a fatal VF, at some point in the next few years.

In practice, RD may be used in combination with one or more other parameters, such as the wall motion index, to predict a group of patients that are at high risk and likely to benefit from ICD implantation, and a group that are low risk group and for which ICD implantation might not be beneficial. In particular, RD may act as a deciding factor in cases where the other parameters fail to point to a clear and unambiguous course of action.

Obtaining HRV through determination of RD, according to the method of the present invention, provides a efficient and improved tool of diagnosis and prognosis in comparison to other ways of obtaining HRV known in the art. In pilot studies RD has demonstrated a negative predictive value of approximately 96% for sudden cardiovascular death, i.e. a prediction that there would not be a fatal VT/VF incident in the next five years was correct approximately 96% of the time. Accordingly, RD may be used as a helpful risk factor in determining which post AMI patients should or should not be treated with an ICD.

In another example application, the patient may have an implanted ICD that is programmed to perform the RD calculation of the present invention. As noted, the inventor has discovered that HRV obtained in the course of continuous patient monitoring can be used to provide advance warning of an imminent VT. This in turn enables the physician or the patient to take preventive or cautionary measures in order to avoid a VT/VF episode or to make it more tolerable. Accordingly, unlike conventional ICD applications which detect VT only as it is unfolding, an ICD equipped with the method of the present invention can use HRV to detect a likely episode of VT at a substantive period of time in advance of the actual episode. As a result, instead of only being able to treat VT after it has already started, the present invention can be used to prevent a VT episode from even occurring that would otherwise have been inevitable.

The RD parameter, used in the described way, has been found to provide early warning of an imminent VT in approximately 60% of the episodes.

In some embodiments of the invention, the early notice provided by the warning occurred between about five minutes to two hours prior to the episode. In some embodiments of the invention, ICD memory holds about two hours of information, or about 8000 heartbeat intervals, and accordingly two hours is about the earliest advance notice that may be obtained while still retaining the data supporting the prognosis of imminent VT. As technology improves, programming techniques are applied, and/or ICD memory size increases, greater advance notice may be possible.

Upon detection of imminent VT, a range of treatment options may be undertaken. In some embodiments, the ICD may apply a remedial electric shock or pacing of the heart. Since the VT episode is not happening immediately but at a later time, the ICD may be able to implement a degree of pacing that is more gradual and less stressful to the patient. Alternatively or additionally, and as shown in modules 42 and 43 of FIG. 2, an alarm may be delivered to the patient, such as by small electric shock, and/or an anti-arrhythmic drug may be automatically injected to suppress or prevent the threatening VT or VF If automatic injection is not available, the patient may heed the warning by going to a hospital to receive an injection, or to wait for the VT in an environment where emergency assistance is available. It is to be appreciated that if a patient has advance notice, even if the ICD eventually delivers a defillibrator shock, the experience may be less painful or jarring since it will not be unexpected as is the case with a conventional ICD. Another possible option is for a suitably equipped ICD to repeat the small warning shock on a periodic basis until it receives patient acknowledgment. This may be useful in cases where the imminent VT is detected while the patient is sleeping, so that the patient is not aware of the warning shock.

In some applications of the invention, continuous monitoring may be performed by an external ECG recorder. For example, patients who have had an AMI are often kept for observation in a hospital for a few weeks after the incident. Such patients will likely not have an ICD, but are at risk of experiencing a dangerous VT/VF. These patients may be hooked up to an ECG programmed to apply the continuous monitoring embodiment of the present invention. Upon detection of an imminent VT, an alarm may be sounded or an electronic message sent to the attention of nearby medical personnel, who can then quickly attend to the patient to administer a drug or other treatment. In a similar manner, the present invention may be used with a Holter recording device.

As the foregoing illustrates, embodiments of the present invention provide a new method of measuring heart rate variability that is based on the relative density of data points. The method is easy to calculate as it is based on the simple counting of data points, unlike conventional methods which make use of relatively complicated algorithms for analysis. The method of measurement is accordingly relatively quick, and provides results sufficiently accurate for clinical use. Applications of the method include diagnosis and prognosis of medical conditions based on pre-recorded heartbeat data, and assistance in the decision whether to implant an ICD. Continuous patient monitoring devices such as ICD's can operate the method of the present invention, and can use the method to obtain advance warning of an imminent episode of VT to enable appropriate treatment to be administered in a timely manner.

Although selected embodiment(s) of the present invention has/have been shown and described, it is to be understood that the present invention is not limited to the described embodiment(s). Instead, it is to be appreciated that changes may be made to this/these embodiment(s) without departing from the principles and spirit of the invention, the scope of which is defined by the claims and the equivalents thereof.

The invention claimed is:

1. A system for measuring heart rate variability (HRV), the system comprising:
    a data generator to receive heartbeat information of a subject, the heartbeat information recorded by a data collector, said heartbeat information representing a series of heart beat intervals corresponding to said subject, said data generator is further to generate a plurality of data points based on the heartbeat information in the form of a two-dimensional representation having a coordinate system including a first axis and a second axis;
    a data analyzer to identify two subsets of data points from said plurality of data points, said two subsets including a first subset of data points within a first axis-interval of said first axis, and a second subset of data points within a second axis-interval of said second axis;
    a processor to calculate a subject-specific heart rate variability (HRV) relative density parameter (RD) value by dividing a first factor, which is based on said first subset of data points by a second factor, which is based on the second subset of data points; and
    an output device, to output the subject-specific HRV RD value.

2. The system for measuring heart rate variability (HRV) according to claim 1, wherein the output device is at least one device selected from the group consisting of: a screen, to display the subject-specific HRV RD value, a printer to print the subject-specific HRV RD value, an alarm to raise an audible sound, and an injector, to deliver an injection to a patient.

3. The system of claim 1, wherein said subject-specific HRV RD value is configured to be compared to at least one predefined reference value corresponding to a heart condition, wherein a relationship between the subject-specific HRV RD value and the reference value is to represent a risk of said subject to suffer from said heart condition.

4. The system of claim 3, wherein said subject-specific HRV RD value comprises a subject-specific dy/dx value, and said reference value comprises a reference dy/dx value.

5. The system of claim 4, wherein said reference dy/dx value is lesser than 2.3.

6. The system of claim 4, wherein said reference dy/dx value comprises a diagnostic dy/dx value configured to be compared to said subject-specific dy/dx value to diagnose said heart condition.

7. The system of claim 4, wherein said reference dy/dx value comprises a prognostic dy/dx value configured to be compared to said subject-specific dy/dx value to provide a prognosis of said heart condition.

8. The system of claim 3, wherein said heart condition comprises congestive heart failure.

9. The system of claim 3, wherein said heart condition comprises Ventricular Tachcardia (VT).

10. The system of claim 1, wherein one factor of said first and second factors comprises a dx factor and another factor of said first and second factors comprises a dy factor, the dx factor corresponding to an x-axis of a Cartesian coordinate system and the dy factor corresponding to a y-axis of the Cartesian coordinate system.

11. The system of claim 10, wherein said dx factor is based on a first number of points within said first axis-interval, said first axis-interval comprises an interval along said x-axis having a maximal number of points compared to other axis-intervals along said x-axis, and wherein said dy factor is based on a second number of points within said second axis-interval, said second axis-interval comprises an interval along said y-axis having a maximal number of points compared to other axis-intervals along said y-axis.

12. The system of claim 1, wherein said subject-specific HRV RD value is equal to the quotient of said first and second factor values.

13. A computer-based method for measuring heart rate variability (HRV), the method comprising:
receiving, by a computing device, heartbeat information of a subject, the heartbeat information recorded by a data collector, said heartbeat information representing a series of heart beat intervals corresponding to said subject;
generating, by said computing device, a plurality of data points based on the heartbeat information in the form of a two-dimensional representation having a coordinate system including a first axis and a second axis;
identifying, by said computing device, two subsets of data points from said plurality of data points, said two subsets including a first subset of data points within a first axis-interval of said first axis, and a second subset of data points within a second axis-interval of said second axis;
calculating, by said computing device, a subject-specific heart rate variability (HRV) relative density parameter (RD) value by dividing a first factor, which is based on said first subset of data points by a second factor, which is based on the second subset of data points; and
outputting the subject-specific HRV RD value.

14. The method of claim 13, wherein said subject-specific HRV RD value is configured to be compared to at least one predefined reference value corresponding to a heart condition, wherein a relationship between the subject-specific HRV RD value and the reference value is to represent a risk of said subject to suffer from said heart condition.

15. The method of claim 14, wherein said subject-specific HRV RD value comprises a subject-specific dy/dx value, and said reference value comprises a reference dy/dx value.

16. The method of claim 15, wherein said reference dy/dx value is lesser than 2.3.

17. The method of claim 15, wherein said reference dy/dx value comprises a diagnostic dy/dx value configured to be compared to said subject-specific dy/dx value to diagnose said heart condition.

18. The method of claim 13, wherein one factor of said first and second factors comprises a dx factor and another factor of said first and second factors comprises a dy factor, the dx factor corresponding to an x-axis of a Cartesian coordinate system and the dy factor corresponding to a y-axis of the Cartesian coordinate system.

19. The method of claim 18, wherein said dx factor is based on a first number of points within said first axis-interval, said first axis-interval comprises an interval along said x-axis having a maximal number of points compared to other axis-intervals along said x-axis, and wherein said dy factor is based on a second number of points within said second axis-interval, said second axis-interval comprises an interval along said y-axis having a maximal number of points compared to other axis-intervals along said y-axis.

20. The method of claim 13, wherein said subject-specific HRV RD value is equal to the quotient of said first and second factor values.

* * * * *